(12) United States Patent
Puskas

(10) Patent No.: US 6,778,854 B2
(45) Date of Patent: Aug. 17, 2004

(54) METHODS OF INDIRECTLY STIMULATING THE VAGUS NERVE WITH AN ELECTRICAL FIELD

(76) Inventor: John D. Puskas, 854 Carlron Ridge, Atlanta, GA (US) 30342

(*) Notice: Subject to any disclaimer, the term of this patent is extended or adjusted under 35 U.S.C. 154(b) by 0 days.

(21) Appl. No.: 10/051,758

(22) Filed: Jan. 16, 2002

(65) Prior Publication Data

US 2002/0198571 A1 Dec. 26, 2002

Related U.S. Application Data

(62) Division of application No. 09/716,783, filed on Nov. 20, 2000, now Pat. No. 6,429,217, which is a division of application No. 09/139,442, filed on Aug. 25, 1998, now Pat. No. 6,479,523.
(60) Provisional application No. 60/072,284, filed on Jan. 23, 1998, and provisional application No. 60/056,994, filed on Aug. 26, 1997.

(51) Int. Cl.[7] ................................................. A61N 1/00
(52) U.S. Cl. ........................................................ 607/2
(58) Field of Search ................................. 600/372–373, 600/377, 380–381; 607/1–3, 42, 9, 115, 116, 118, 124; 128/897–898

(56) References Cited

U.S. PATENT DOCUMENTS

| | | | | |
|---|---|---|---|---|
| 4,351,330 A | * | 9/1982 | Scarberry | 128/207.15 |
| 5,179,952 A | * | 1/1993 | Buinevicius et al. | 600/380 |
| 5,379,765 A | * | 1/1995 | Kajiwara et al. | 600/380 |
| 5,651,378 A | | 7/1997 | Matheny et al. | |
| 5,668,117 A | | 9/1997 | Shapiro | |
| 5,889,033 A | | 3/1999 | Kaminski | |
| 5,913,876 A | * | 6/1999 | Taylor et al. | 607/2 |
| 6,043,273 A | | 3/2000 | Duhaylongsod | |
| 6,060,454 A | | 5/2000 | Duhaylongsod | |
| 6,087,394 A | | 7/2000 | Duhaylongsod | |
| 6,101,412 A | | 8/2000 | Duhaylongsod | |
| 6,127,410 A | | 10/2000 | Duhaylongsod | |
| 6,141,589 A | | 10/2000 | Duhaylongsod | |
| 6,234,985 B1 | * | 5/2001 | Lurie et al. | 601/41 |

FOREIGN PATENT DOCUMENTS

| | | |
|---|---|---|
| AU | 9890156 | 8/1998 |
| EP | 1051168 | 11/2000 |
| WO | WO 9907354 | 2/1999 |

OTHER PUBLICATIONS

Bufkin, et al., "Controlled Intermittent Asystole: Pharmacologic Potentiation of Vagal–Induced Asystole," *Ann. Thorac. Surg.*, 1998;66: pp. 1185–1190.
DiPiro, et al., "Pharmacotherapy: A Pathophysiologic Approach;" Elsevier, New York; pp. 153–157, (1989).
Goodman and Gilman's, *The Pharmacological Basis of Therapeutics* (6th Ed.), MacMillan Publishing Co., Inc., New York, pp. 93–94 and 104–108 (1980).
Matheny, et al., "Vagus Nerve Stimulation as a Method to Temporarily Slow or Arrest the Heart," *Ann. Thorac. Surg.*, 1997:63: pp. 528–529.
Thompson, et al., "Bradycardia Induced by Intravascular Versus Direct Stimulation of the Vagus Nerve," *Ann. Thorac. Surg.*, 1998;65: 637–42.

* cited by examiner

*Primary Examiner*—Kennedy Schaetzle
*Assistant Examiner*—Kristen Droesch
(74) *Attorney, Agent, or Firm*—Kilpatrick Stockton LLP

(57) ABSTRACT

A method for indirectly stimulating a vagus nerve of a patient includes the steps of positioning one or more electrodes in the vicinity of the vagus nerve and then actuating the electrode(s) to create an electrical field for stimulating the vagus nerve. Disclosed embodiments include positioning one or more electrodes in the esophagus, trachea, or jugular vein, on the neck of the patient, and combinations thereof.

51 Claims, 5 Drawing Sheets

METHODS OF INDIRECTLY STIMULATING THE VAGUS NERVE WITH AN ELECTRICAL FIELD

CROSS-REFERENCE TO RELATED APPLICATIONS

This application is a divisional of U.S. patent application Ser. No. 09/716,783, filed Nov. 20, 2000, now U.S. Pat. No. 6,429,217, which is a divisional of U.S. patent application Ser. No. 09/139,442, filed Aug. 25, 1998, now U.S. Pat. No. 6,479,523, which claims priority to U.S. Provisional Application Ser. No. 60/072,284, filed Jan. 23, 1998 and U.S. Provisional Application No. 60/056,994, filed Aug. 26, 1997.

BACKGROUND OF THE INVENTION

Minimally invasive direct coronary artery bypass (MIDCAB) surgery, both via sternotomy and alternative incisions, is a substantially revolutionary development in surgery for allowing bypass surgery to be conducted on a beating heart. However, beating heart surgery shows an undesirably higher rate of early graft failure than conventional coronary artery bypass procedures using cardiopulmonary bypass and cardioplegia. The technical difficulty of sewing the coronary artery anastomosis on a beating heart is likely an important factor in this difference in outcome between the two techniques. Controlled intermittent asystole (CIA) during brief intervals required for placing anastomotic sutures is suitable for improving the precision of coronary anastomoses performed on a beating heart and reducing graft failure while increasing ease of operation.

Cardiopulmonary bypass (CPB) and chemical arrest using cardioplegia solutions have traditionally provided surgeons with optimal operative conditions: hemodynamic control and cardiac quiescence. This optimal field has contributed to technical success in increasingly complex cardiac surgical operations. However, there has been recent interest in performing coronary artery bypass surgery without either complete cardiopulmonary bypass or cardioplegia. The quality of the distal anastomosis is a primary concern among cardiac surgeons who observe and perform coronary artery bypass graft (CABG) procedures unaided by cardioplegic arrest and cardiopulmonary bypass. Coronary artery bypass graft failure rates reported with minimally invasive direct coronary artery bypass range from 3.8 to 8.9%, while traditional CABG on CPB has a reported anastomotic failure rate of 0.12%. This may reflect a difference in anastomotic precision between MIDCAB and CPB-aided CABG. Although the benefits of avoiding extracorporeal circulation and global cardioplegia in beating heart procedures are important, they do not outweigh the performance of an optimal coronary anastomosis.

The key difference in the anastomotic results between conventional CABG and beating heart CABG is related to achieving elective asystole during construction of the distal anastomosis. Cardiac motion can be minimized during MIDCAB procedures via pharmacologic bradycardia (adenosine, β blockade) and mechanical stabilization using various devices. Although these techniques do improve operative conditions, they only approximate the advantages of elective asystole achieved with CPB and cardioplegia.

Applicants show that a state of controlled intermittent asystole (CIA) is produced off CPB, which provides a major advantage otherwise gained by cardioplegic arrest on CPB. In particular, CIA is achieved using unilateral (or bilateral) vagus nerve stimulation coupled with pharmacologic suppression of electromechanical escape activity.

Applicants demonstrate that elective, controlled intermittent asystole is produced by vagus nerve stimulation after treatment with an acetylcholinesterase inhibitor, a β-adrenergic receptor blocker, or a calcium channel blocker, or combinations thereof.

Figure 1:
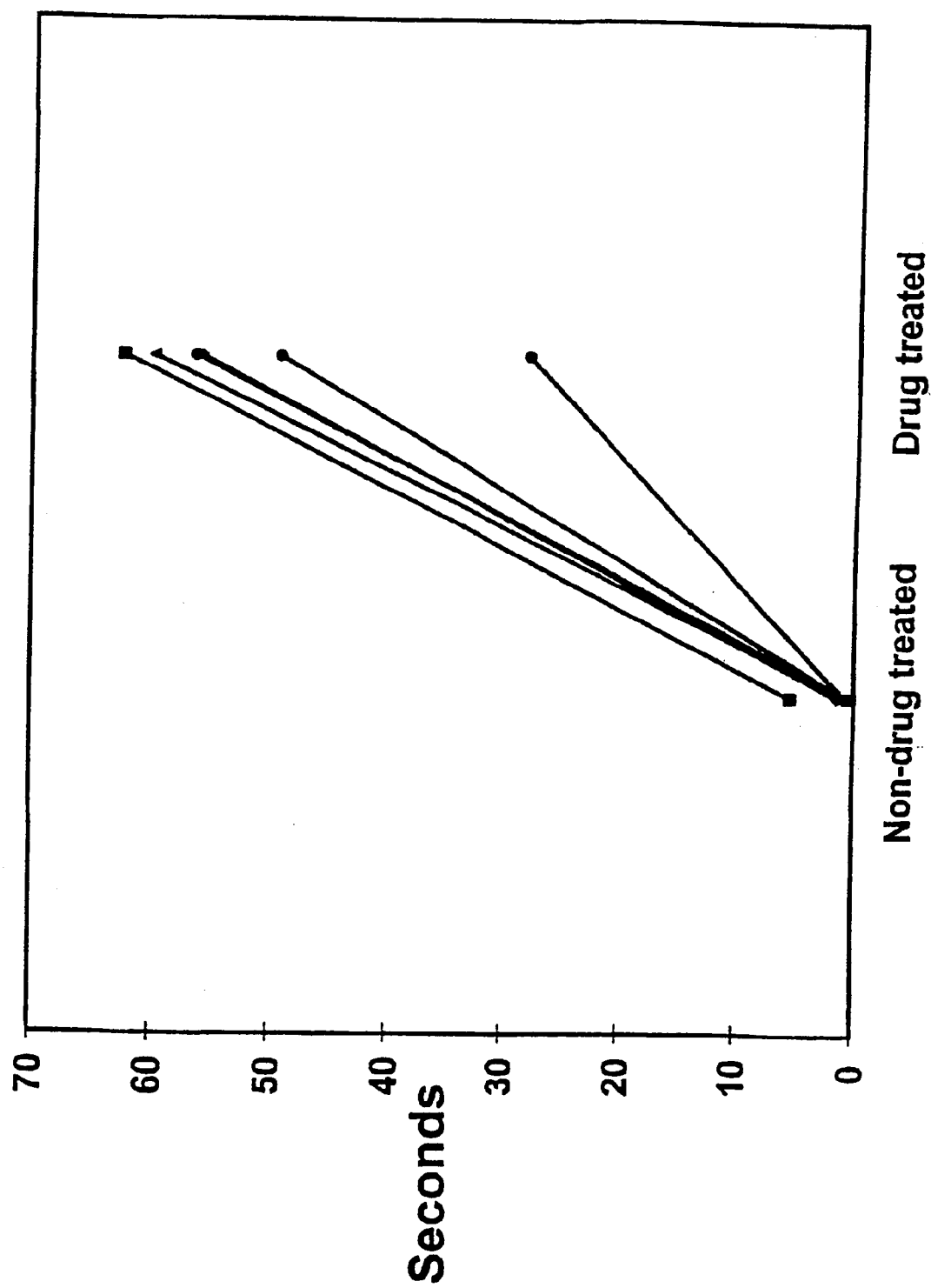
FIG. 1 Duration of asystole achieved during 60 second vagal stimulation. Lines connect the periods of asystole observed in the non-drug treated and drug treated states in each experimental animal. Drug administration lengthened significantly the period of asystole.

| Abbreviations and Definitions | |
|---|---|
| CABG | Coronary artery bypass graft |
| CIA | Controlled intermittent asystole |
| CPB | Cardiopulmonary bypass |
| MIDCAB | Minimally invasive direct coronary artery bypass; intended to include any CABG without the use of global cardioplegia; synonymous with beating heart surgery, irrespective of incision |

DETAILED DESCRIPTION OF THE INVENTION

Increased acetylcholine activity by acetylcholinesterase inhibition and prevention of electromechanical escape activity by β-adrenergic receptor and calcium channel blockade during vagal stimulation produces a marked potentiation of vagal-induced asystole and a means of achieving CIA. CIA achieved by pharmacologic potentiation of vagal-induced asystole is a suitable technique to facilitate MIDCAB operations. In particular, anastomoses and other complex suturing is facilitated during such controlled asystolic events, a readily appreciated advantage in surgery involving minimally invasive direct coronary artery bypass operations on a beating heart. CIA might have particular advantages in partially or totally endoscopic CABG, and possibly in percutaneous or surgical transmyocardial laser revascularization.

The present invention provides a pharmaceutical composition, comprising an acetylcholinesterase inhibitor, a β-adrenergic receptor blocker, and a calcium channel blocker, said composition useful for performing beating heart surgery. The invention also provides that the composition is useful for controlled intermittent asystole in minimally invasive direct coronary artery bypass surgery. The invention further provides that the compositions can be administered in combination with vagus nerve stimulation. Vagus nerve stimulation can be achieved by direct or indirect electrical stimulation.

In preferred independent embodiments, the acetylcholinesterase inhibitor can be pyridostygmine bromide, the β-adrenergic receptor blocker can be propranolol hydrochloride, and the calcium channel blocker can be verapamil bromide.

The invention also provides a pharmaceutical composition, comprising an acetylcholinesterase inhibitor and a β-adrenergic receptor blocker, said composition useful for performing beating heart surgery. In preferred embodiments, the acetylcholinesterase inhibitor can be pyridostygmine bromide, and the β-adrenergic receptor blocker can be propranolol hydrochloride. The invention also provides that the composition is useful for controlled intermittent asystole in minimally invasive direct coronary artery bypass surgery. The invention further provides that the compositions can be administered in combination with vagus nerve stimulation. Vagus nerve stimulation can be achieved by direct or indirect electrical stimulation.

The invention also provides a pharmaceutical composition, comprising an acetylcholinesterase inhibitor and a calcium channel blocker, said composition useful for performing beating heart surgery. In preferred embodiments, the acetylcholinesterase inhibitor can be pyridostygmine bromide, and the calcium channel blocker can be verapamil bromide. The invention also provides that the composition is useful for controlled intermittent asystole in minimally invasive direct coronary artery bypass surgery. The invention further provides that the compositions can be administered in combination with vagus nerve stimulation. Vagus nerve stimulation can be achieved by direct or indirect electrical stimulation.

The principal challenge of beating heart CABG surgery has been to recreate the advantageous operative conditions of a quiescent operative field provided during conventional CABG with CPB and cardioplegic arrest. A variety of pharmacologic manipulations and mechanical stabilizing techniques assist in performing CABG off pump. These interventions to date minimize, but do not eliminate, cardiac motion. The concept that a state of controlled intermittent asystole improves the conditions for construction of distal coronary artery bypass anastomosis in non-CPB assisted cases was demonstrated by applicant. CIA is defined as operator-initiated and controlled intervals of mechanical cardiac standstill. These intervals may be timed to coincide with placement of sutures in the anastomosis, after which normal cardiac rhythm and hemodynamics are restored while preparations are made for the next successive stitch. Experiments reported by the applicant indicate that the minor bradycardia known to be produced by vagus nerve stimulation is dramatically augmented to function as an electromechanical "on-off switch" by pharmalogical inhibition of acetylcholinesterase and blockade of β-adrenergic receptors and calcium channels. Controlled intermittent asystole may prove equally useful for CPB-assisted cardiac surgery without global cardioplegia.

The chronotropic effects of vagal nerve stimulation have been well described and typically produce an initial pause followed by a "vagal escape" beat and sustained bradycardia during continuous optimal stimulation of the vagus nerve. Cardiac responses to a 60 second vagal stimulation without adjunctive therapy achieved an average pause of 1.6 seconds terminated by vagal escape beats with a 19% reduction in heart rate. Vagus nerve stimulation alone did not produce a controlled period of asystole desired for CIA. In contrast, a triple pharmacologic regimen of e.g, pyridostigmine, propranolol and verapamil inhibited vagal escape, and allowed sustained periods of asystole lasting up to 60 seconds and sequential asystoles of 15 seconds each. Sequential asystoles had no significant hemodynamic consequences.

It is apparent that suppression of the electromechanical escape during vagal stimulation is necessary to produce a sufficient interval of asystole to allow a single stitch to be reliably placed during construction of a distal CABG anastomosis. The negative chronotropic effects of vagal stimulation are produced by acetylcholine release. Acetylcholine activity may be enhanced by inhibition of acetylcholinesterase activity by agents such as pyridostigmine. Additionally, it is known that calcium channel blockade by e.g. verapamil potentiates the negative chronotropic effect of vagus nerve stimulation. Another component in electromechanical escape may be related to increased catecholamine activity in the sympathetic nervous system, triggered by hypotension. Catecholamines increase the rate of diastolic depolarization and decrease the threshold potential. β-adrenergic receptor blockade via e.g. propranolol reduces the effects of catecholamine activity and facilitates suppression of electromechanical escape.

Administration of this combination therapy produced a significant reduction in heart rate and maximum developed ventricular pressure along with an increase in left ventricular end-diastolic pressure, but did not alter mean arterial pressure. There was no apparent fatigue of this pharmacologic effect after sequential stimulations. The animals used for pilot experiments appeared to tolerate this pharmacologic regimen without other adverse hemodynamic side effects, such as acidosis.

The short-term hemodynamic effects of a single prolonged stimulation were found to be substantially insignificant. Likewise the metabolic consequences as detected by pH and changes in base deficit were insignificant.

The pharmacologic regimen used in this investigation sustained the period of vagal-induced asystole for about sixty seconds. This interval would allow more than sufficient time for construction of a distal CABG anastomosis. Animals followed for two hours after administration of drugs displayed responses to vagal stimulation similar to those in the non-drug treated state, confirming reversibility of the drug effects.

An untoward effect of the pharmacologic regimen which requires consideration before clinical application is vagal-induced secretions. All animals displayed significant salivation after initiation of vagal stimulation. However, there were no problems with oxygenation and ventilation due to tracheobronchial secretions in these experiments. Vagal-induced oropharyngeal and tracheobronchial secretions are pertinent in the clinical setting. Additionally, the effects on recurrent laryngeal nerve function require consideration.

Evidence suggests that the long-term effects of this regimen on the vagus nerve are not harmful. Chronic vagus nerve stimulation has been utilized as therapy for intractable seizure disorders without apparent nerve injury or impaired function. Applicants have shown that vagal-mediated chronotropic control at two hours after completion of the experimental protocol was similar to the non-drug treated state.

In summary, controlled intermittent asystole can be achieved by potentiation of vagal-induced asystole via a pharmacologic combination of e.g, propranolol and verapamil for suppression of electromechanical escape and e.g, pyridostigmine for acetylcholinesterase inhibition. Asystole can be reproducibly achieved for prolonged intervals and for shorter multiple sequential intervals using this technique.

Nerve Stimulation

To achieve consistent asystole, applicants have found that nerve stimulation of the right vagus nerve before or after treatment with the pharmacological combinations of the present invention is preferred.

Electrical stimulation is carried out on the right vagus nerve, preferably at a site on the neck. Other suitable locations for vagus nerve stimulation include, but are not limited to, unipolar or bipolar electrical stimulation of the right or left vagus, or both, stimulation of the vagus in the chest after sternotomy, stimulation with a percutaneous catheter or electrode probe in the internal jugular vein, esophagus, or trachea, or combination of these. The nerve stimulator is typically a Grass wire with a single point of contact, but other suitable stimulators include a pair of pacing wires or electrodes placed about 1 cm apart to allow bipolar prodromic stimulation. A single continuous impulse is applied of between about 5 seconds to about 90 seconds, preferably between about 5 seconds and about 15 seconds, to allow a single stitch during surgery. Impulse parameters can readily be varied, e.g., a frequency range of between about 1 Hz and about 500 Hz, preferably between about 20 Hz to about 80 Hz, more preferably about 40 Hz, with an amplitude between about 1 to about 40 volts.

Pharmacologic Potentiation

The acetylcholinesterase inhibitor is also known as a cholinesterase inhibitor. Suitable acetylcholinesterase inhibitors include, but are not limited to tacrine hydrochloride, pyridostigmine bromide, neostigmine methylsulfate, and edrophonium chloride. One preferred acetylcholinesterase inhibitor is pyridostigmine bromide. Acetylcholinesterase inhibitors are administered in a dosage range between about 0.01 mg/kg and about 100 mg/kg, preferably between about 0.1 mg/kg and about 2.0 mg/kg, more preferably about 0.5 mg/kg.

The beta-adrenergic receptor blocker is also known as a beta-adrenergic blocking agent. Suitable beta-adrenergic receptor blockers include, but are not limited to, sotalol HCl, timolol maleate, esmolol hydrochloride, carteolol hydrochloride, propranolol hydrochloride, betaxolol hydrochloride, penbutolol sulfate, metoprolol tartrate, acetbutolol hydrochloride, the combination of atenolol and chlorthalidone, metoprolol succinate, pindolol, and bisoprolol fumarate. One preferred beta-adrenergic receptor blocker is propranolol hydrochloride. Beta-adrenergic receptor blockers are administered in a dosage range between about 0.01 mg/kg and about 100 mg/kg, preferably between about 0.1 mg/kg and about 2.0 mg/kg, more preferably about 80 µg/kg.

Suitable calcium channel blockers include, but are not limited to, nifedipine, nicardipine hydrochloride, diltiazem HCl, isradipine, verapamil hydrochloride, nimodinpine, amlodipine besylate, felodipine, bepridil hydrochloride, and nisoldipine. One prefererred calcium channel blocker is verapamil hydrochloride. Calcium channel blockers are administered in a dosage range of between about 0.001 mg/kg to about 1 mg/kg, preferably between about 0.01 mg/kg and about 0.2 mg/kg, more preferably about 50 µg/kg.

It will be understood that other dosage combinations may be effective. The appropriate dosage is determined by the age, weight, sex, health status of the patient, and may vary with a variety of other factors according to conventional clinical practice.

EXAMPLE 1

Experimental Preparation

The sheep in the examples of the present invention received humane care in compliance with "Principles of Laboratory Animal Care" formulated by the National Society for Medical Research and the "Guide for Care and Use of Laboratory Animals" prepared by the National Academy of Sciences and published by the National Institutes of Health (NIH Publication No. 80-23, revised 1985). The experimental protocol was approved by the Institutional Animal Care and Use Committee of Emory University.

Seven sheep weighing 44 to 45 kg were premedicated with xylazine (0.1 mg/kg) and atropine (0.2 mg/kg) 30 minutes prior to induction of anesthesia with intravenous thiopental (2.2 mg/kg) and lidocaine (2.2 mg/kg). The animals were endotracheally intubated and placed on a volume ventilator with isoflurane for maintenance of anesthesia. Limb leads and precordial lead were placed for electrocardiographic monitoring. The right femoral artery was cannulated for arterial pressure and arterial blood gas monitoring. Tidal volume was adjusted to 10 cc/kg and a rate of 12 breaths per minute, with adjustments made to maintain pH at 7.35–7.45, pO2 greater than 100 mm Hg, and pCO2 between 35–45 mm Hg.

A right cervical incision was performed, the vagus nerve was carefully isolated, and a nerve stimulation probe (Harvard Apparatus, South Natick, Mass.) was placed on the nerve. A median sternotomy was made to expose the heart. A high-fidelity solid-state micromanometer (Millar Inc, Houston, Tex.) was secured in the ascending aorta for aortic blood pressure monitoring. An additional micromanometer was introduced into the left ventricle through the apex for left ventricular pressure monitoring.

EXAMPLE 2

Experimental Protocol

Each animal underwent vagal stimulation before and after drug administration. The pharmacologic regimen consisted of pyridostigmine (0.5 mg/kg) for acetylcholinesterase inhibition, propranolol (80 µg/kg) for β-adrenergic receptor blockade, and verapamil (50 µg/kg) for calcium channel blockade. Vagal stimulation was performed with a nerve stimulator (Grass Instrument Co, Quincy, Mass.) in the monopolar mode at a frequency of 40 Hz, an impulse duration of 0.4 msec, and an amplitude of 2–6 volts. Vagal stimulations were delivered in two regiments: 1) continuous 60 second impulse and 2) sequential 15 second impulses. The continuous 60 second stimulation was designed to determine the longevity of vagal-induced asystole and the physiologic effects of prolonged vagal-induced hypotension. Sequential 15 second vagal stimulations were performed to simulate the suturing intervals required for graft anastomoses and to determine whether cardiac fatigue, electromechanical escape, and physiologic effects occurred under these practical conditions.

EXAMPLE 3

Data Acquisition and Analysis

Electrocardiographic and hemodynamic data were gathered via an analog-to-digital conversion board (Data Translation, Inc, Marlboro, Mass.) and processed, stored, and analyzed via a microprocessor personal 486 computer (Compaq Computer Corp, Houston, Tex.) using interactive proprietary software (Spectrum™, Triton Technology, San Diego, Calif.). The system was configured to collect 4 channels of physiologic data at a frequency of 50 Hz (sufficient for slow-wave waveforms and mean pressure data) over a 200 second period that encompassed the 60 second stimulation or the sequential 15 second train of stimulations. The software allowed subsequent videographic display and analysis of the hemodynamic data.

EXAMPLE 4

Results

Before drug administration, vagal stimulation for 60 seconds produced a brief pause in electromechanical activity (1.6±0.9 seconds) followed by vagal escape and resumption of sinus rhythm with a reduction in heart rate by 19.4±11.9% compared to pre-stimulation heart rate. Similarly, sequential 15 second vagal stimulation performed to stimulate the suturing intervals required for CABG anastomoses produced a short pause (1.1±0.4 seconds) followed by vagal escape and sinus rhythm with a reduction in heart rate of 37±6%.

Administration of the pharmacologic regimen (propranolol, verapamil, pyridostigmine) reduced the heart rate and increased the left ventricular end diastolic pressure, but did not affect the mean arterial pressure or maximum dP/dt as shown in Table 1.

TABLE 1

Hemodynamics before and after drug treatment

|  | Before drugs (mean ± SEM) | After drugs (mean ± SEM) | p value (paired t test) |
| --- | --- | --- | --- |
| Heart rate (bpm) | 114 ± 4 | 87 ± 4 | 0.002 |
| MAP (mm Hg) | 84 ± 5 | 84 ± 5 | NS |
| dP/dt max (mm Hg/sec) | 3286 ± 232 | 2847 ± 140 | NS |
| LVEDP (mm HG) | 3.9 ± 0.5 | 7.3 ± 0.9 | 0.005 | bpm - beats per minute; dP/dt max - maximum developed left ventricular pressure; LVEDP - left ventricular end diastolic pressure; MAP - mean aortic pressure; NS - not significant; SEM - standard error of the mean; sec - seconds.

Figure 2:
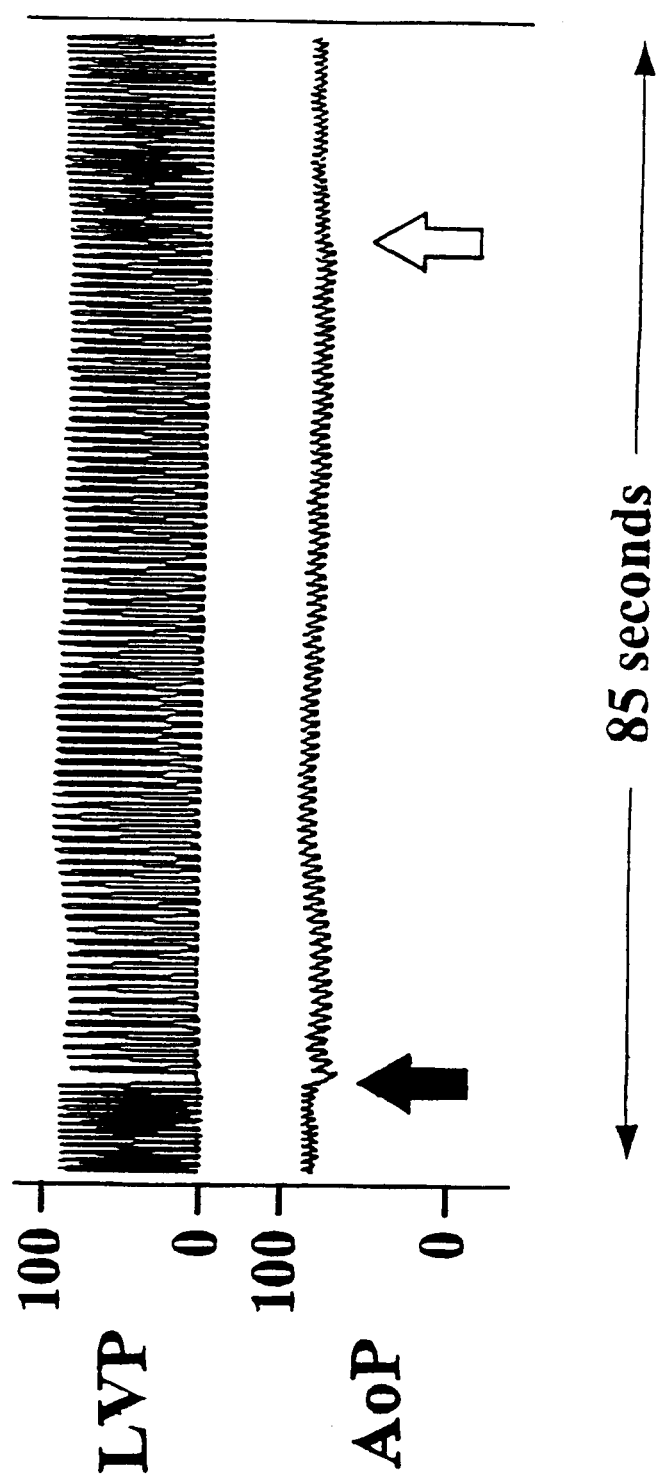
FIG. 2. Representative left ventricular and aortic pressure tracings during 60 second vagal stimulation in the non-drug treated (A) and drug treated states (B). Dark and open arrows mark the initiation and termination of the vagal impulse, respectively. Before drug treatment, a short pause followed by escape and bradycardia was observed during the 60 second impulse. After drug treatment, prolonged asystole occurred during the 60 second impulse with return of mechanical function after termination. lvp—left ventricular pressure; aop—aortic pressure.
Figure 2:
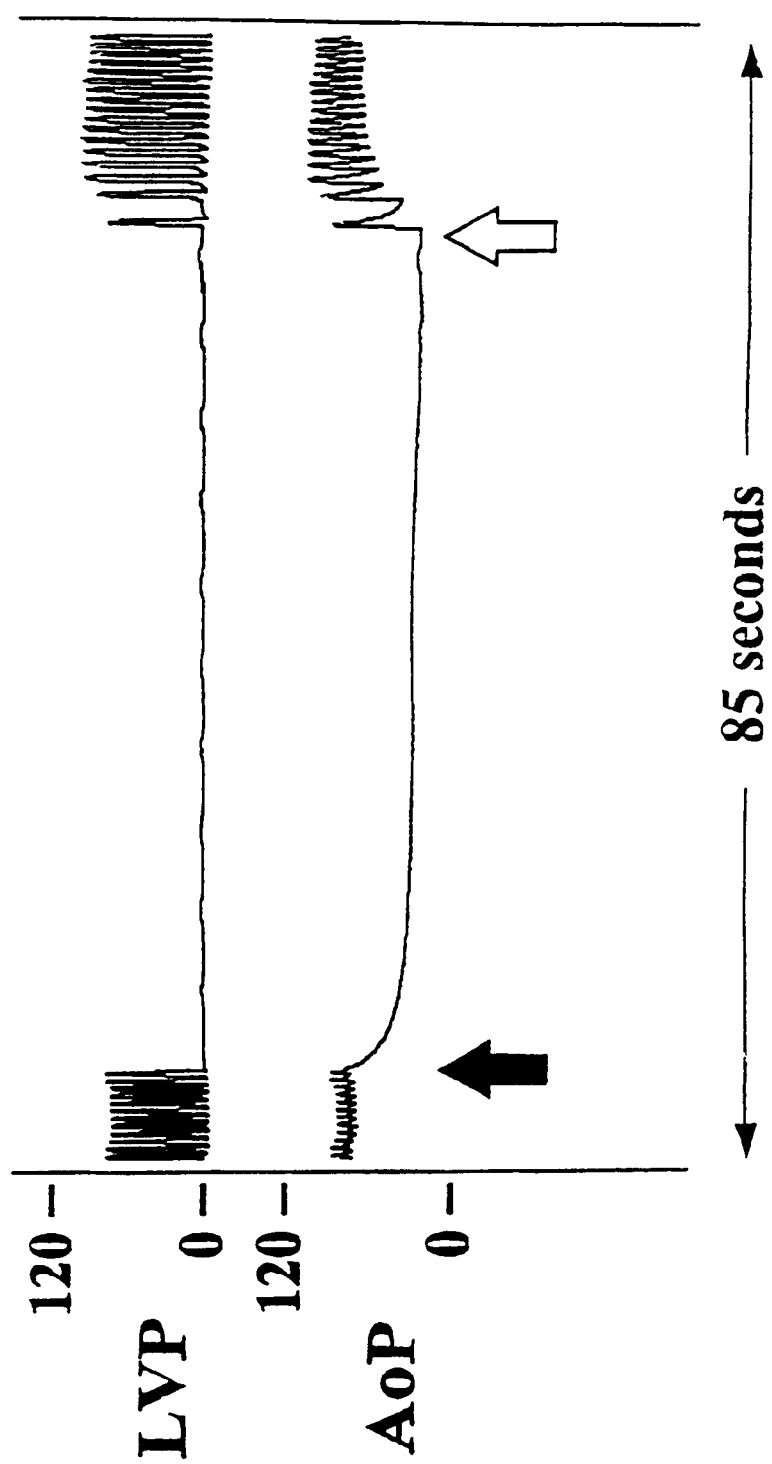

After drug administration, 60 second vagal stimulation produced asystole averaging 52±5.6 seconds. The individual responses of the animals before and after drug administration are shown in FIG. 1. Six animals achieved controlled asystole. Five of these six achieved controlled asystole for greater than 50 seconds. The effects of 60 second vagal stimulation before and after drug treatment in responsive animals are contrasted by representative left ventricular and aortic pressure tracings are shown for a representative experiment in FIG. 2. Before drug regimen treated, vagal stimulation produced no appreciable change in cardiac rhythm or hemodynamics. In contrast, the triple drug regimen facilitated a consistent asystole and circulatory arrest until the stimulus was withdrawn, after which hemodynamics were rapidly restored to pre-stimulation values. The prolonged asystole and circulatory arrest produced no significant differences in the hemodynamic parameters measured before and after drug-aided 60 second vagal stimulation (Table 2).

TABLE 2

Hemodynamics pre- and post-asystole produced by 60 second stimulation after drug treatment

|  | Pre-asystole (mean ± SEM) | Post-asystole (mean ± SEM) | p value (paired t test) |
| --- | --- | --- | --- |
| Heart rate bpm) | 91 ± 8 | 87 ± 7 | NS |
| MAP (mm Hg) | 86 ± 6 | 92 ± 6 | NS |

TABLE 2-continued

Hemodynamics pre- and post-asystole produced by 60 second stimulation after drug treatment

|  | Pre-asystole (mean ± SEM) | Post-asystole (mean ± SEM) | p value (paired t test) |
| --- | --- | --- | --- |
| dP/dt max (mm Hg/sec) | 3032 ± 182 | 3223 ± 212 | NS |
| LVEDP (mmHg) | 5.8 ± 1.0 | 6.0 ± 0.8 | NS | bpm - beats per minute; dP/dt max - maximum developed left ventricular pressure; LVEDP - left ventricular end diastolic pressure; MAP - mean aortic pressure; NS - not significant; SEM - standard error of the mean; sec - seconds.

Likewise there was no difference in the parameters measured by arterial blood gases at one and five minutes after the 60 second stimulation compared to pre-stimulation values (Table 3).

TABLE 3

Arterial blood gas data pre-, 1 minute post-, and 5 minutes post-systole produced by 60 second stimulation after drug treatment

|  |  | Post-asystole | | |
| --- | --- | --- | --- | --- |
|  | Pre-asystole (mean ± SEM) | 1 minute (mean ± SEM) | 5 minutes (mean ± SEM) | p p value (ANOVA) |
| pH | 7.42 ± 0.03 | 7.40 ± 0.03 | 7.42 ± 0.03 | NS |
| PCO$_2$ (mm Hg) | 41 ± 4 | 42 ± 4 | 40 ± 4 | NS |
| PO$_2$ (mm Hg) | 377 ± 87 | 380 ± 75 | 390 ± 83 | NS |
| HCO$_3$ (mEq/L) | 26 ± 1 | 26 ± 1 | 26 ± 1 | NS |
| Base excess (mEq/L) | 1.2 ± 0.7 | 1.0 ± 0.4 | 1.3 ± 0.5 | NS |

ANOVA - one-way analysis of variance with repeated measures; NS - not significant; SEM - standard error of the mean.

Figure 3:
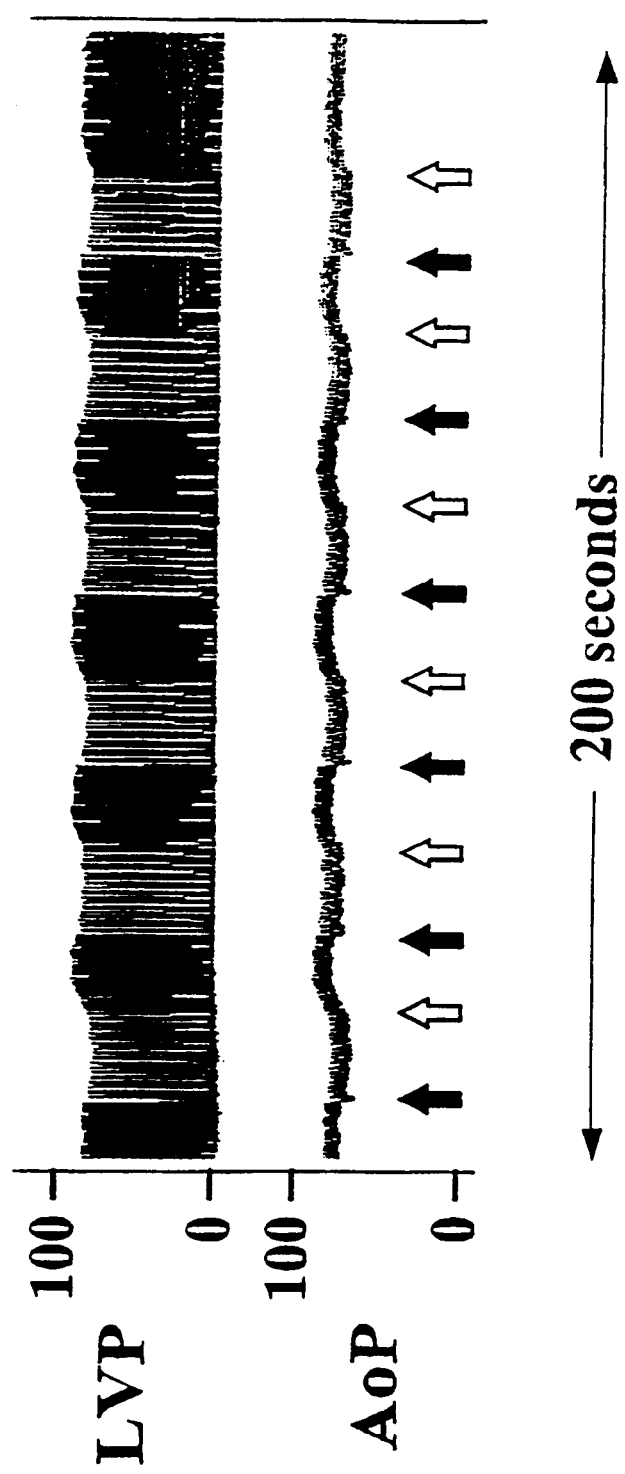
FIG. 3. Representative left ventricular and aortic pressure tracings during sequential 15 second vagal stimulations in the non-drug treated (A) and drug treated states (B). Dark and open arrows mark the initiation and termination of the vagal impulses, respectively. Before drug treatment, each 15 second stimulation produced a short pause followed by bradycardia, while after drug treatment, asystole lasted the duration of each 15 second stimulation. lvp—left ventricular pressure; aop—aortic pressure.
Figure 3:
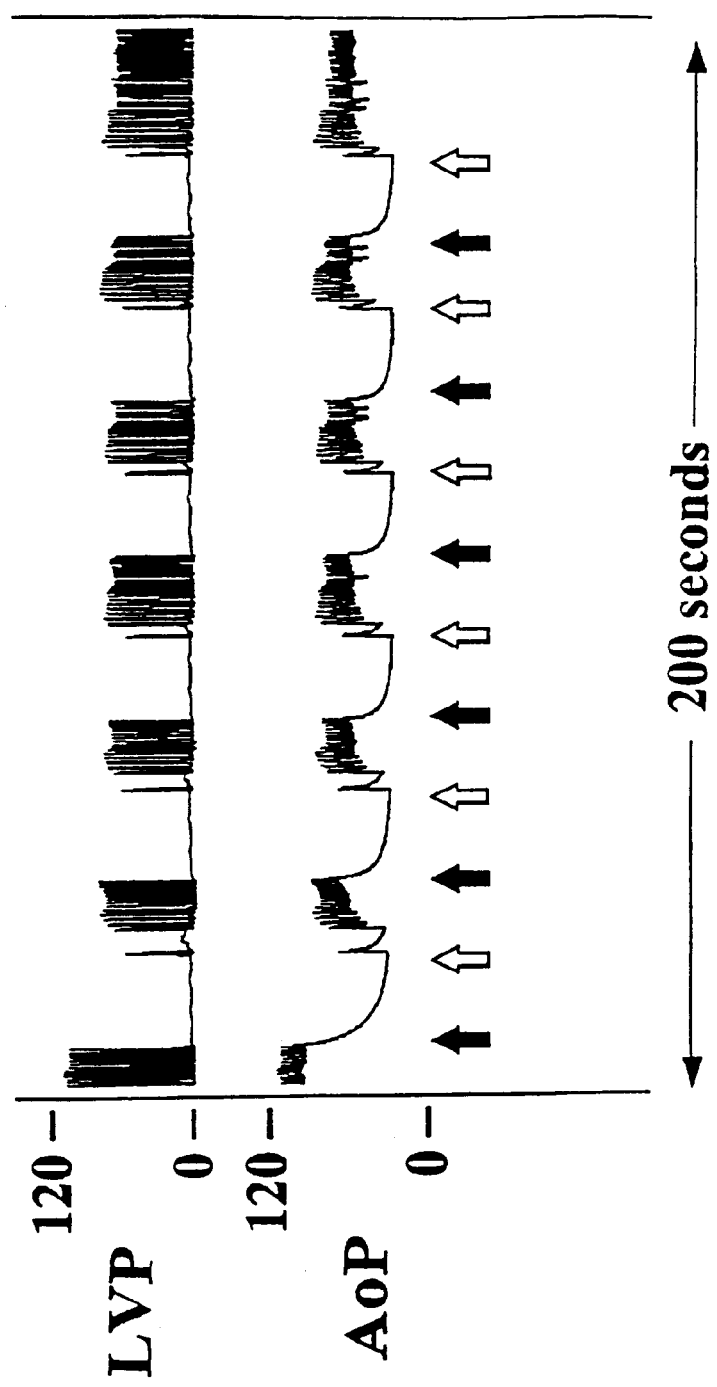

Five to six sequential 15 second vagal stimulations in the drug treated state produced consistent and stable asystole (FIG. 3). Three of the six animals had a single escape beat during one of the 15 second stimulations. The other three displayed complete asystole during each of the 15 second stimulations. A sustained cardiac rhythm began an average of 5.3±1.8 seconds after termination of each 15 second impulse during which interval a single beat was often observed immediately after withdrawal of stimulation.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A method for stimulating a vagus nerve of a patient, comprising the steps of:

inserting an electrode into the trachea of said patient; and actuating said electrode to create an electrical field effective to stimulate said vagus nerve;

wherein said step of inserting an electrode into the trachea of said patient comprises the step of inserting a first electrode into the trachea of said patient;

wherein said method comprises the further step of inserting a second electrode into the trachea of said patient in spaced apart relation to said first electrode; and wherein said step of actuating said electrode to create an electrical field comprises the step of actuating at least one of said first and second electrodes to create an electrical field.

2. The method of claim 1, wherein said step of inserting a second electrode into the trachea of said patient in spaced apart relation to said first electrode comprises the step of inserting a second electrode into the trachea of said patient approximately one centimeter from said first electrode.

3. The method of claim 1, wherein said step of actuating at least one of said electrodes to create an electrical field comprises the step of actuating both of said first and second electrodes to create an electrical field.

4. The method of claim 1, wherein said step of actuating at least one of said electrodes to create an electrical field comprises the step of actuating one or both of said electrodes in one of a unipolar or a bipolar mode.

5. The method of claim 1, wherein said vagus nerve is stimulated for a period of between about five and about ninety seconds.

6. The method of claim 5, wherein said vagus nerve is stimulated for a period of between about five and about fifteen seconds.

7. The method of claim 1, wherein said step of actuating said electrode to create an electrical field comprises the step of applying an impulse at a frequency of between about one Hertz and about five hundred Hertz.

8. The method of claim 7, wherein said step of applying an impulse at a frequency of between about one Hertz and about five hundred Hertz comprises the step of applying an impulse at a frequency of between about twenty Hertz and about eighty Hertz.

9. The method of claim 8, wherein said step of applying an impulse at a frequency of between about twenty Hertz and about eighty Hertz comprises the step of applying an impulse at a frequency of about forty Hertz.

10. The method of claim 1, wherein said step of actuating said electrode to create an electrical field comprises the step of actuating said electrode to generate electrical impulses having a duration of 0.4 msec.

11. The method of claim 1, wherein said step of actuating said electrode to create an electrical field comprises the step of transmitting to said electrode an electrical impulse having an amplitude of from about one to about forty volts.

12. The method of claim 11, wherein said step of actuating said electrode to create an electrical field comprises the step of transmitting to said electrode an electrical impulse having an amplitude of from about two to about six volts.

13. The method of claim 1, wherein said step of actuating said electrode to create an electrical field effective to stimulate said vagus nerve comprises the step of creating an electrical field effective to stimulate said vagus nerve to achieve asystole.

14. A method for stimulating a vagus nerve of a patient, comprising the steps of:
inserting a first electrode into the esophagus of said patient;
inserting a second electrode into the trachea of said patient; and
actuating at least one of said electrodes to create an electrical field which stimulates said vagus nerve;
wherein said step of inserting a second electrode into the trachea of said patient comprises the step of inserting a second electrode into the trachea of said patient to a location approximately one centimeter from said first electrode in said esophagus of said patient.

15. The method of claim 14, wherein said vagus nerve is stimulated for a period of between about five and about ninety seconds.

16. The method of claim 15, wherein said vagus nerve is stimulated for a period of between about five and about fifteen seconds.

17. The method of claim 14, wherein said step of actuating at least one of said electrodes to create an electrical field comprises the step of applying an impulse to at least one of said electrodes at a frequency of between about one Hertz and about five hundred Hertz.

18. The method of claim 17, wherein said step of applying an impulse at a frequency of between about one Hertz and about five hundred Hertz comprises the step of applying an impulse at a frequency of between about twenty Hertz and about eighty Hertz.

19. The method of claim 18, wherein said step of applying an impulse at a frequency of between about twenty Hertz and about eighty Hertz comprises the step of applying an impulse at a frequency of about forty Hertz.

20. The method of claim 14, wherein said step of actuating at least one of said electrodes to create an electrical field comprises the step of actuating at least one of said electrodes to generate electrical impulses having a duration of 0.4 msec.

21. The method of claim 14, wherein said step of actuating at least one of said electrodes to create an electrical field comprises the step of transmitting to at least one of said electrodes an electrical impulse having an amplitude of from about one to about forty volts.

22. The method of claim 21, wherein said step of actuating at least one of said electrodes to create an electrical field comprises the step of transmitting to at least one of said electrodes an electrical impulse having an amplitude of from about two to about six volts.

23. The method of claim 14, wherein said step of actuating said electrode to create an electrical field effective to stimulate said vagus nerve comprises the step of creating an electrical field effective to stimulate said vagus nerve to achieve asystole.

24. A method for stimulating a vagus nerve of a patient, comprising the steps of:
inserting a first electrode into the trachea of said patient;
inserting a second electrode into a jugular vein of said patient; and
actuating at least one of said electrodes to create an electrical field which stimulates said vagus nerve.

25. The method of claim 24, wherein said step of inserting a second electrode into a jugular vein of said patient comprises the step of inserting a second electrode into a jugular vein of said patient to a location approximately one centimeter from said first electrode in said trachea of said patient.

26. The method of claim 24, wherein said step of actuating at least one of said electrodes to create an electrical field comprises the step of actuating both of said first and second electrodes to create an electrical field.

27. The method of claim 24, wherein said step of actuating at least one of said electrodes to create an electrical field comprises the step of actuating one or both of said electrodes in one of a unipolar or a bipolar mode.

28. The method of claim 24, wherein said vagus nerve is stimulated for a period of between about five and about ninety seconds.

29. The method of claim 28, wherein said vagus nerve is stimulated for a period of between about five and about fifteen seconds.

30. The method of claim 24, wherein said step of actuating at least one of said electrodes to create an electrical field comprises the step of applying an impulse to at least one of said electrodes at a frequency of between about one Hertz and about five hundred Hertz.

31. The method of claim 30, wherein said step of applying an impulse at a frequency of between about one Hertz and about five hundred Hertz comprises the step of applying an impulse at a frequency of between about twenty Hertz and about eighty Hertz.

32. The method of claim 31, wherein said step of applying an impulse at a frequency of between about twenty Hertz and about eighty Hertz comprises the step of applying an impulse at a frequency of about forty Hertz.

33. The method of claim 24, wherein said step of actuating at least one of said electrodes to create an electrical field comprises the step of actuating at least one of said electrodes to generate electrical impulses having a duration of 0.4 msec.

34. The method of claim 24, wherein said step of actuating at least one of said electrodes to create an electrical field comprises the step of transmitting to at least one of said electrodes an electrical impulse having an amplitude of from about one to about forty volts.

35. The method of claim 34, wherein said step of actuating at least one of said electrodes to create an electrical field comprises the step of transmitting to at least one of said electrodes an electrical impulse having an amplitude of from about two to about six volts.

36. The method of claim 24, wherein said vagus nerve is stimulated during a surgical procedure selected from the group consisting of: minimally invasive direct coronary artery bypass graft surgery, off-pump coronary artery bypass graft surgery, coronary artery bypass surgery performed on cardiopulmonary bypass, partially or totally endoscopic coronary artery bypass graft surgery, percutaneous or surgical transmyocardial laser revascularization procedure, or a surgical procedure performed upon a heart, heart valves, myocardium, coronary vascular structure, peripheral vascular structure, a electrophysiological procedure, a neurosurgical procedure, or a percutaneous transcatheter coronary procedure.

37. The method of claim 24, wherein said step of actuating said electrode to create an electrical field effective to stimulate said vagus nerve comprises the step of creating an electrical field effective to stimulate said vagus nerve to achieve asystole.

38. A method for stimulating a vagus nerve of a patient, comprising the steps of:
    inserting a first electrode into the trachea of said patient;
    placing a second electrode on the neck of said patient; and
    actuating at least one of said electrodes to create an electrical field which stimulates said vagus nerve.

39. The method of claim 38, wherein said step of positioning a second electrode on the neck of said patient comprises the step of positioning a second electrode on the neck of said patient at a location approximately one centimeter from said first electrode in said trachea of said patient.

40. The method of claim 38, wherein said step of actuating at least one of said electrodes to create an electrical field comprises the step of actuating both of said first and second electrodes to create an electrical field.

41. The method of claim 38, wherein said step of actuating at least one of said electrodes to create an electrical field comprises the step of actuating one or both of said electrodes in one of a unipolar or a bipolar mode.

42. The method of claim 38, wherein said vagus nerve is stimulated for a period of between about five and about ninety seconds.

43. The method of claim 42, wherein said vagus nerve is stimulated for a period of between about five and about fifteen seconds.

44. The method of claim 38, wherein said step of actuating at least one of said electrodes to create an electrical field comprises the step of applying an impulse to at least one of said electrodes at a frequency of between about one Hertz and about five hundred Hertz.

45. The method of claim 44, wherein said step of applying an impulse at a frequency of between about one Hertz and about five hundred Hertz comprises the step of applying an impulse at a frequency of between about twenty Hertz and about eighty Hertz.

46. The method of claim 45, wherein said step of applying an impulse at a frequency of between about twenty Hertz and about eighty Hertz comprises the step of applying an impulse at a frequency of about forty Hertz.

47. The method of claim 38, wherein said step of actuating at least one of said electrodes to create an electrical field comprises the step of actuating at least one of said electrodes to generate electrical impulses having a duration of 0.4 msec.

48. The method of claim 38, wherein said step of actuating at least one of said electrodes to create an electrical field comprises the step of transmitting to at least one of said electrodes an electrical impulse having an amplitude of from about one to about forty volts.

49. The method of claim 48, wherein said step of actuating at least one of said electrodes to create an electrical field comprises the step of transmitting to at least one of said electrodes an electrical impulse having an amplitude of from about two to about six volts.

50. The method of claim 38, wherein said vagus nerve is stimulated during a surgical procedure selected from the group consisting of: minimally invasive direct coronary artery bypass graft surgery, off-pump coronary artery bypass graft surgery, coronary artery bypass surgery performed on cardiopulmonary bypass, partially or totally endoscopic coronary artery bypass graft surgery, percutaneous or surgical transmyocardial laser revascularization procedure, or a surgical procedure performed upon a heart, heart valves, myocardium, coronary vascular structure, peripheral vascular structure, a electrophysiological procedure, a neurosurgical procedure, or a percutaneous transcatheter coronary procedure.

51. The method of claim 38, wherein said step of actuating said electrode to create an electrical field effective to stimulate said vagus nerve comprises the step of creating an electrical field effective to stimulate said vagus nerve to achieve asystole.

* * * * *